United States Patent [19]
Dawson et al.

[11] Patent Number: 5,891,993
[45] Date of Patent: Apr. 6, 1999

[54] TEMPLATE ASSEMBLED SYNTHETIC PROTEIN

[75] Inventors: Philip E. Dawson; Stephen B.H. Kent, both of La Jolla, Calif.

[73] Assignee: The Scripps Research Institute, La Jolla, Calif.

[21] Appl. No.: 586,764

[22] PCT Filed: Aug. 11, 1994

[86] PCT No.: PCT/US94/09165

§ 371 Date: Jan. 29, 1996

§ 102(e) Date: Jan. 29, 1996

[87] PCT Pub. No.: WO95/04543

PCT Pub. Date: Feb. 16, 1995

[51] Int. Cl.$^6$ .......................................................... C07K 7/02
[52] U.S. Cl. ........................... 530/323; 530/332; 530/324; 530/333; 530/339; 530/345

[58] Field of Search .................................. 514/2; 530/345, 530/332, 333, 339, 324

[56] References Cited

PUBLICATIONS

Schnolzer, Science 256, 221, 1992.
Mutter, Angewante Chemie (Int'l Ed.) 28, 535–554, 1989.
Futaki, Tetrahedron Lett 38, 6237, 1997.

*Primary Examiner*—Cecilia J. Tsang
*Assistant Examiner*—David Lukton
*Attorney, Agent, or Firm*—Donald G. Lewis

[57] ABSTRACT

Disclosed herein are template assembled synthetic protein (TASP) molecules that contain dendritic linkage units having the structure $\psi$ ($CO$—$S$—$CH_2$—$CO$—$NH$). Also disclosed are methods of preparing the template assembled synthetic proteins.

12 Claims, 4 Drawing Sheets

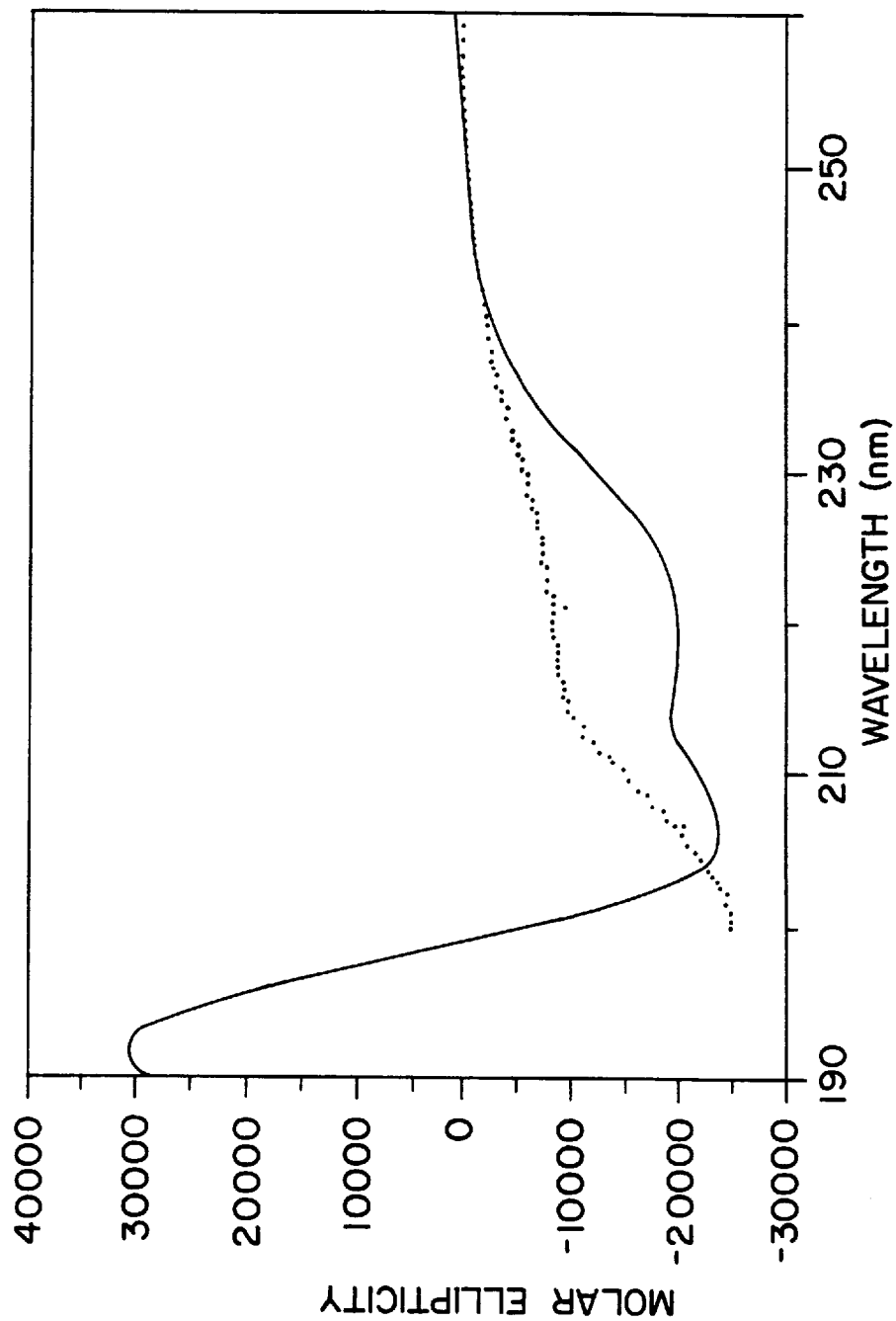

TEMPLATE ASSEMBLED SYNTHETIC PROTEIN

TECHNICAL FIELD

The invention relates to the synthesis of branched or dendritic peptides. More particularly, the invention relates to the synthesis of template assembled synthetic protein (TASP) molecules using chemoselective ligation procedures and to the genus of TASP's which employ dendritic linkage units having the structure ψ(CO—S—$CH_2$—CO—NH).

BACKGROUND ART

Since the time of Emil Fischer, it has been a goal of organic chemists to design and chemically synthesize proteins. In recent years there has been a growing interest in the de novo design of proteins, particularly helix-bundle proteins, and their production by means of chemical synthesis or recDNA-expression. Examples of helix-bundle proteins designed de novo are provided by M. Hecht et al. (*Science*, 1990, vol. 249, pages 884–891), by L. Regan et al. (*Science*, 1988, vol. 241, pages 976–978), by W. F. DeGrado et al. (*Science*, 1989, vol. 243, pages 622–628), and by N. E. Zhou et al. (*Biochemistry*, 1992, vol. 31, pages 5739–5746).

In some cases, unexpected results have been obtained in which the experimentally observed structure of synthetic helix bundles has been different than the intended structure because of the uncontrolled nature of non-covalent intermolecular association, e.g., see B. Lovejoy et al. (*Science*, 1993, vol. 259, pages 1288–1293). To avoid such problems, helix bundle proteins have been made by the preparation of covalent arrays linked through porphyrin molecules or through metal chelate complexes. Preliminary evidence indicates that the expected structures have been achieved, e.g., see T. Sasaki et al. (*J. Am. Chem. Soc.*, 1989, vol. 111, pages 380–381) and R. M. Ghadiri et al. (*J. Am. Chem. Soc.*, 1992, vol. 114, pages 4000–4002).

An alternative, earlier approach to the preparation of covalent peptide arrays of predetermined secondary and tertiary structure is the "template assembled synthetic protein" (TASP) concept, disclosed by M. Mutter (*Peptides-Chemistry and Biology, Proceedings of the 10th American Peptide Symposium*; Marshall, G. R., Ed.; Escom: Leiden, 1988; pages 349–353). A template molecule is used to covalently anchor arrays of secondary structural elements. The distinctive feature of the TASP approach is the nonlinear topology used; the molecule is made up of an array of branched polypeptides, rather than the folded linear polypeptide chain of natural proteins, e.g., M. Mutter et al., (*Angew. Chem.*, Int. Ed. Engl., 1989, vol. 28, pages 535–554). It is anticipated that this elegant concept will have a profound effect on the de novo design of proteins.

However, conventional synthetic approaches for preparing TASP molecular assemblies are arduous and/or provide low yields. For example, both stepwise solid phase synthesis (SPPS) and protected segment condensation approaches have been employed with limited success. M. Mutter, M. et al. (*J. Am. Chem. Soc.*, 1992, vol. 114, pages 1463–1470) discloses an example of a stepwise solid phase synthesis (SPPS) of a template assembled synthetic protein. In addition, B. Dorner et al. (*Innovation and Perspectives in Solid Phase Synthesis*, Roger Epton Ed.; Intercept Limited: Andover, 1992; pages 163–170) and by I. Ernest et al. (*Tetrahedron Lett.*, 1990. vol. 31, pages 4015–4018) disclose examples of the protected segment condensation approach for synthesizing template assembled synthetic proteins. Only a minimal number of TASP molecules have been produced by arduous synthetic efforts, e.g. supra and M. Mutter et al. (*Proteins*, 1989, vol. 5, pages 13–21) and G. Tuchscherer (*Protein Science*, 1992, vol. 1, pages 1377–1386). Despite the exquisite care with which some of these syntheses have been performed, questions still remain with respect to TASP preparations as homogeneous molecular species of defined covalent composition. A convenient, direct general preparation of these molecules in unambiguous fashion would have great utility.

Recently, M. Schnolzer introduced the chemoselective ligation of unprotected peptide segments as a route to the total chemical synthesis of protein analogs of native (i.e. linear) topology (*Science*, 1992, vol. 256, pages 221–225). This approach uses unique, mutually reactive functionalities, one type on each segment, to covalently assemble long chain molecules from completely unprotected peptide segments. In this way, maximal advantage is taken of our ability to synthesize, handle, purify, and characterize unprotected peptides. Solubility problems are reduced and the target molecule is produced directly in the final unprotected form.

DISCLOSURE OF THE INVENTION

The invention employs a chemoselective ligation approach in the synthesis of TASP molecules. The approach used is shown in Scheme I. The TASP is assembled from short unprotected peptide segments, which are synthesized in straightforward fashion by standard methods and which are readily purified to high levels of homogeneity. The target 4-helix TASP molecule was designed on the basis of the work of Mutter (*Tetrahedron*, 1988, vol. 44, pages 771–785). The final molecule contains a total of four copies of the helix-forming peptide 1, one copy attached to the side chain of each of four lysine residues in a template molecule. The template molecule 2 contains a central Gly-Pro sequence to facilitate the formation of a reverse-turn structure, and to thus promote the association of the helix-forming peptides.

Scheme 1
Synthesis of a 4-Helix TASP
by Chemoselective Ligation

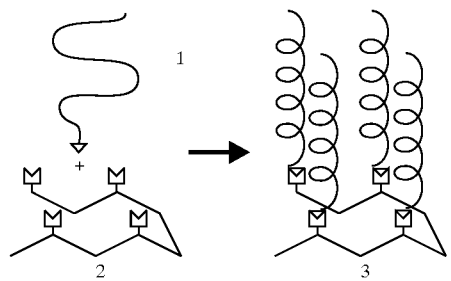

BRIEF DESCRIPTION OF THE DRAWINGS

FIG. 1 (A) illustrates a fourteen residue pro-helix peptide-thiocarboxylate 1, prepared by SPPS on a thioester resin.

FIG. 1 (B) illustrates a nine residue peptide template 2, prepared by SPPS using $N^\alpha$Boc protection and both base- and acid-labile side chain protection to allow differential modification of the side chains. Step (i) employs 50% piperidine in DMF; step (ii) employs bromoacetic anhydride in DCM; step (iii) employs HF/10% p-cresol, 1 hour, 0° C. Details are provided in the Materials and Methods section.

FIG. 2 (A) illustrates an analytical HPLC of the reaction mixture after 5 hours of reaction. Positions and original amounts of the reactants, i.e., the branch peptide (1) and the template peptide (2), are indicated by dashed-line peaks. The product 4-helix TASP (3) is indicated by a solid line. Minor components were identified by ionspray mass spectrometry (MS). Peak "a" is a pro-helix peptide-carboxylate formed by hydrolysis of the athiocarboyxlate. Peak "b" is a (pro-helix)₃(BrAc)₁ template. Peak "c" is a dimer (pro-helix—αCOS—)₂ formed by atmospheric oxidation.

FIG. 2 (B) illustrates an analytical HPLC of the reaction mixture after 70 min. Products are labeled and identified as above.

FIG. 3 (B) illustrates a reconstruction of the total raw MS data to a single charge state.

FIG. 4 illustrates the circular dichroism spectrum in water of the HPLC-purified 4-helix TASP product 3 (solid line). Characteristic minima at 220 nm and 208 nm and a maximum at 193 nm indicate high helical content for the ligated TASP. Under identical conditions the pro-helix peptide 1 (dotted line) gave a weak featureless spectrum with no indication of helical structure.

BEST MODE FOR CARRYING OUT THE INVENTION

Figure 1A:
FIGS. 1 (A) and (B) illustrate examples of unprotected synthetic peptides for use in the TASP synthesis.

The invention is a template assembled synthetic protein (TASP) employing a dendritic linkage unit with a structure ψ(CO—S—CH₂—CO—NH). More particularly, the TASP includes at least one template peptide and one branch peptide joined to one another using the dendritic linkage unit indicated above. The template peptide includes at least one amino acid residue with a template side chain bearing an amino group, preferably a lysine group. The template peptide is coupled to the dendritic linkage unit via the lysine or other side chain bearing an amino group. The branch peptide is coupled to the dendritic linkage unit via its C-terminal. An important aspect of the invention is the chemoselective linkage between the template peptide and the branch peptide, i.e., the structure ψ(CO—S—CH₂—CO—NH) which couples the C-terminal end of the branch peptide to the template peptide via the amino group of the template side chain. The dendritic linkage unit may be schematically illustrated as follows:

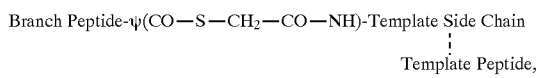
Template Peptide,

The ensemble forms a template assembled synthetic protein (TASP).

In a preferred embodiment, the branch peptide is a pro-helical peptide which, upon incorporation into the template assembled synthetic protein (TASP) and exposure to helix promoting conditions, is capable of assuming a helical configuration. A preferred branch peptide has the following sequence, viz. Seq. 1:

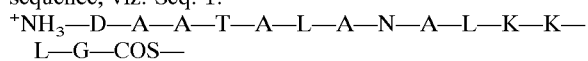

The above branch peptide is a pro-helical peptides which, upon incorporation into a template assembled synthetic protein (TASP) and exposure to helix promoting conditions, is capable of assuming helical configurations. The TASP may include only one branch peptide or may include multiple branch peptides. A preferred TASP includes four branch peptides having Sequence 1. When multiple branch peptides are employed, each branch peptide is coupled to the template peptide via its own dendritic linkage unit.

A preferred template peptide has the following sequence, viz. seq. 2:

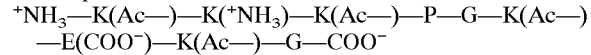

wherein K(Ac—) represents a lysine amino acid residue having an lysine side chain with an acetylated amino group.

The invention also contemplates the process for preparing a template assembled synthetic protein (TASP). The process comprises the following steps:

Step A: providing an unprotected template peptide including an amino acid residue having a side chain bearing an amino group bonded to a haloacetyl functionality;

Step B: providing unprotected branch peptides each bearing a ᵅCOSH moiety at its C-terminal end; and then Step C: combining the unprotected template peptide from said Step A with the unprotected branch peptide of said Step B under nucleophilic reaction conditions for promoting a substitution reaction between the ᵅCOSH moiety of the branch peptides and the haloacetyl functionalities of the template molecule for chemoselectivly ligating the branch peptides to the template peptide and forming the template assembled synthetic protein (TASP).

In a preferred mode of the process, the haloacetyl functionality of the template peptide of Step A is a bromoacetyl group attached to the amino group of a lysine side chain. In Step C, the dendritic linkage unit is formed when the ᵅCOSH moiety of the branch peptides and the bromoacetyl group of the template molecule undergo a nucleophilic substitution reaction to create a dendritic linkage unit having the following structure, viz.:

A preferred mode of the process for preparing a TASP may also include an additional step after completion of the assembly for exposing the reaction product to helix promoting conditions for changing the conformation of the branch peptides into a helical conformation.

EXAMPLE

Figure 1B:
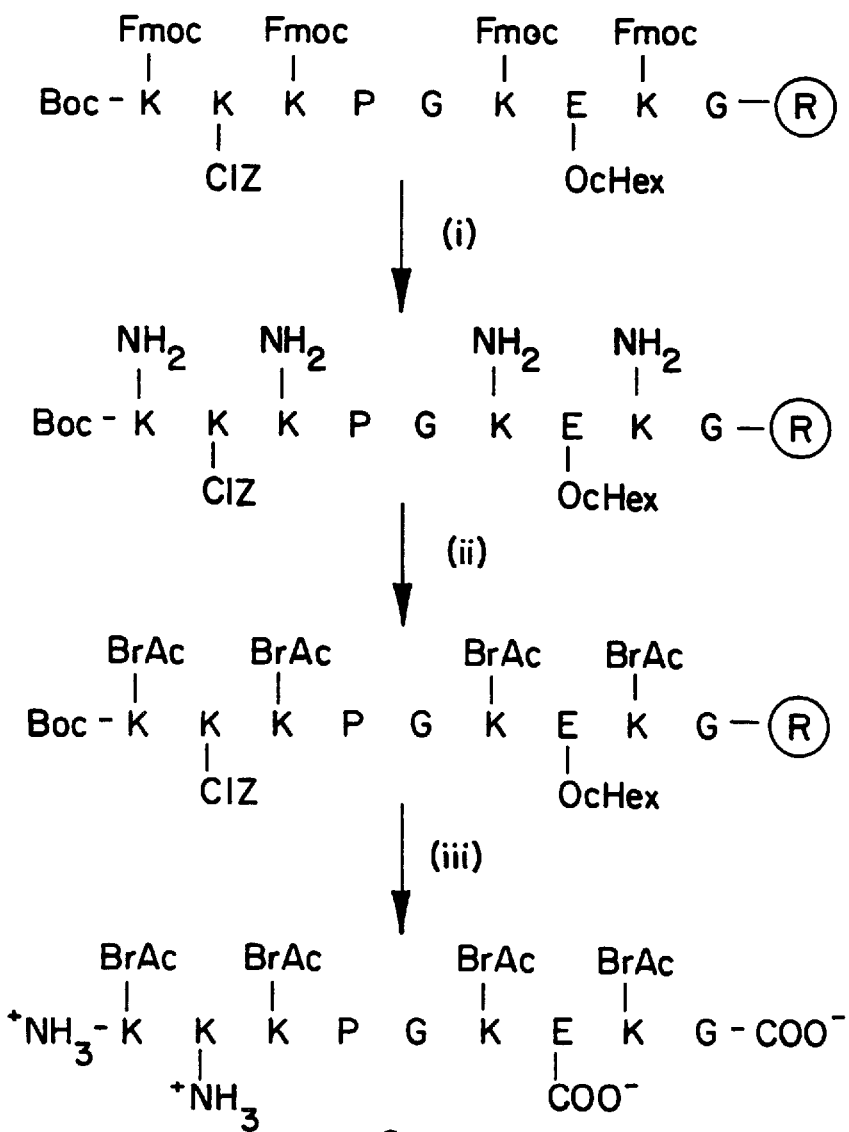

The synthetic peptide 1, intended to form a 13 residue amphipathic helix under suitable helix-promoting conditions, was prepared with an additional C-terminal —GlyᵅCOSH residue (FIG. 1A). This pro-helix peptide was reacted with the template peptide 2 containing four lysine side chains modified to contain bromoacetyl moieties (FIG. 1B). Peptides were chemically synthesized by manual stepwise solid phase methods according to published procedures, e.g., S. B. Kent (*Ann Rev Biochem.,* 1988, vol. 57, pages 957–989) and M. Schnolzer et al. (*Int. J. Peptide Protein Res.,* 1992, vol. 40, pages 180–193). Acidolytic cleavage of the pro-helix peptide from a thioester resin generates the peptide-ᵅCOSH 1, e.g., J. Blake (*Int. J. Peptide Protein Res.,* 1981, vol. 17, pages 273–274) and D. Yamashiro (*J. Int. J. Peptide Protein Res.,* 1988, vol. 31, pages 322). A combination of base-labile and acid-labile protecting groups was used to generate the template molecule 2 with four of the five lysine sidechains modified with bromoacetyl groups (FIG. 1B), e.g., R. A. Robey et al. (*Anal. Biochem.*, 1989, vol. 177, pages 373–377). The range of functionalities present in the two peptides is shown in FIG. 1.

Figure 2A:
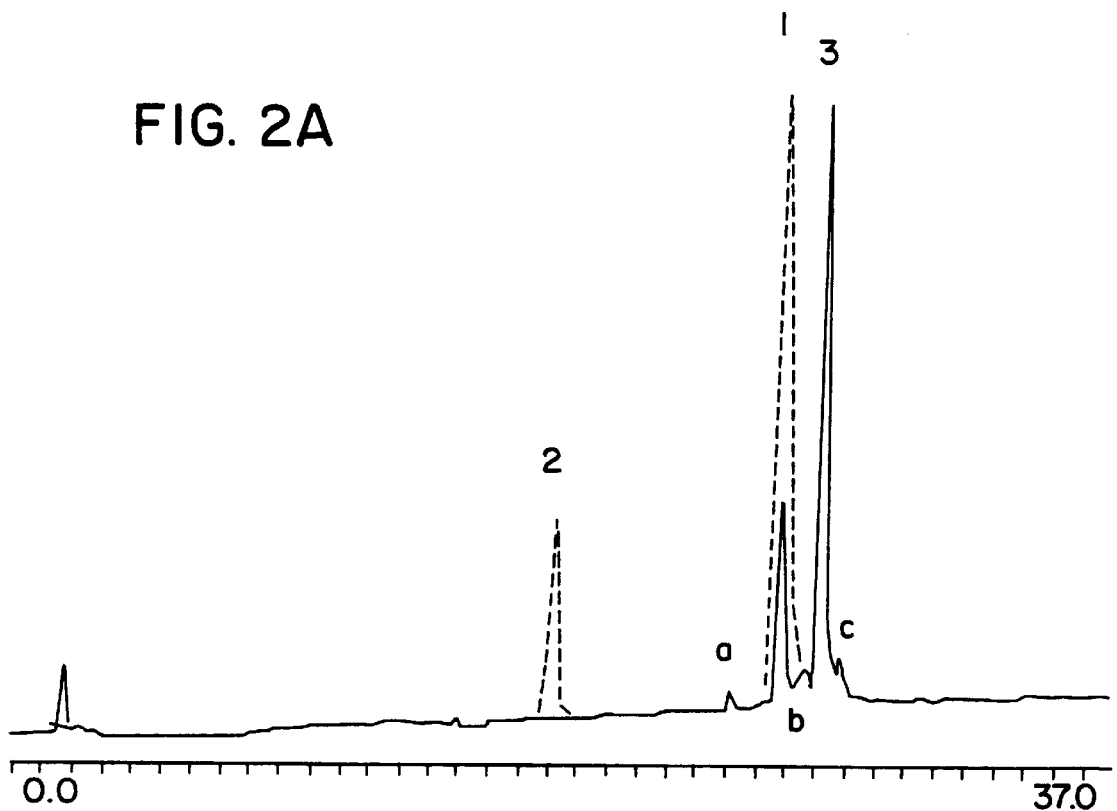
FIGS. 2 (A) and (B) illustrate a reaction of the pro-helix peptide-ᵅthiocarboxylate 1 with the (BrAc) template peptide 2, in aqueous solution at pH 5.
Figure 2B:
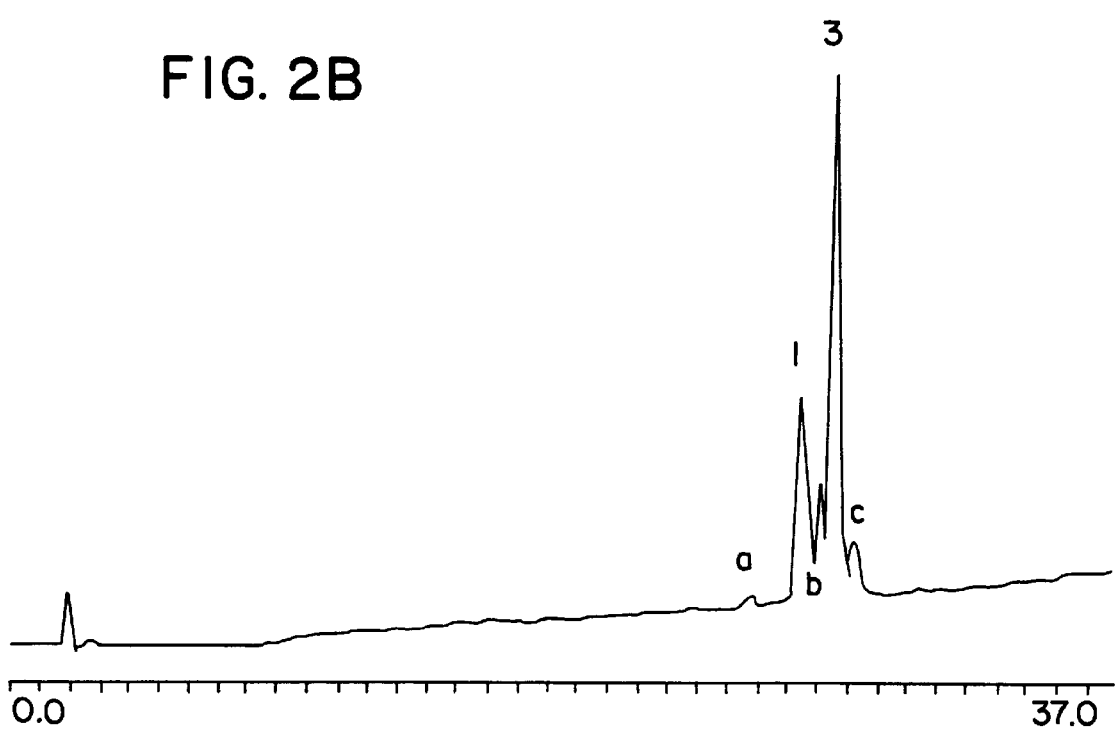

The unprotected peptides were simply ligated in the desired fashion by nucleophilic reaction between the $^\alpha$COSH moiety of the pro-helix peptide 1 and the bromoacetyl functionalities of the template molecule 2. The reaction proceeded cleanly over several hours at ambient temperature in aqueous buffer at pH 5.0 to give a near-quantitative yield of the 4-helix TASP molecule 3 (FIG. 2A). The reaction was monitored by direct ionspray MS of the reaction mixture and by analytical HPLC, e.g., M. Schnolzer (*Anal. Biochem.*, 1992, vol. 204, pages 335–343). Although salts generally interfere with the evaporative ionization process, the dilute $NH_4OAc$ buffer used was compatible with direct ionspray MS of synthetic peptides. An excess of the peptide-$^\alpha$COSH component 1 was used, and the final reaction mixture was fully depleted of the $(BrAc)_4$ template molecule 2. The ligation proceeded very quickly as monitored by HPLC. After just 70 minutes, the reaction had progressed almost to completion (FIG. 2B). In addition to the target 4-helix TASP 3, the only other detectable components were residual excess pro-helix-$^\alpha$COSH 1, residual amounts of (pro-helix)$_3$(BrAc)$_1$ template, and trace amounts of pro-helix-$^\alpha$COOH and the dimer (pro-helix-$^\alpha$COS—)$_2$. It is of some interest that the only intermediate reaction product detected (FIG. 2B) was the (pro-helix)$_3$ (BrAc)$_1$template.

Figure 3A:
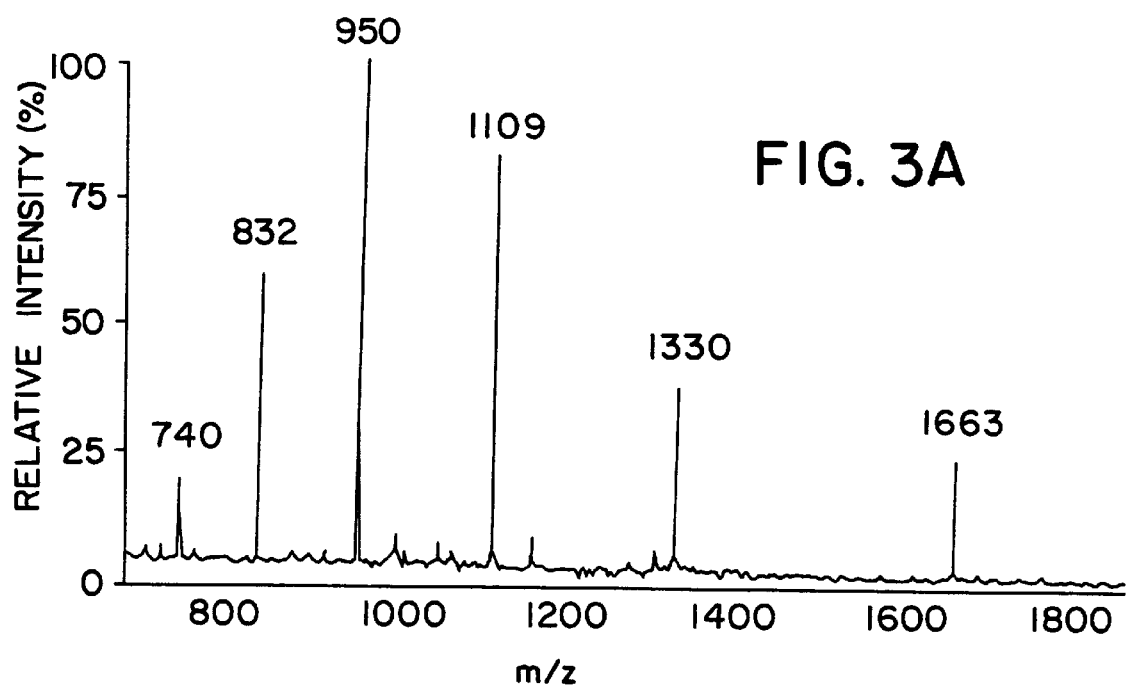
FIG. 3 (A) illustrates the ionspray mass spectrometry (MS) of HPLC-purified peak 3. Raw data is shown. The multiple charge states all arise from protonation of a single molecular species having a molecular weight of 6647 Daltons. No significant other species were detected in the HPLC fraction.
Figure 3B:
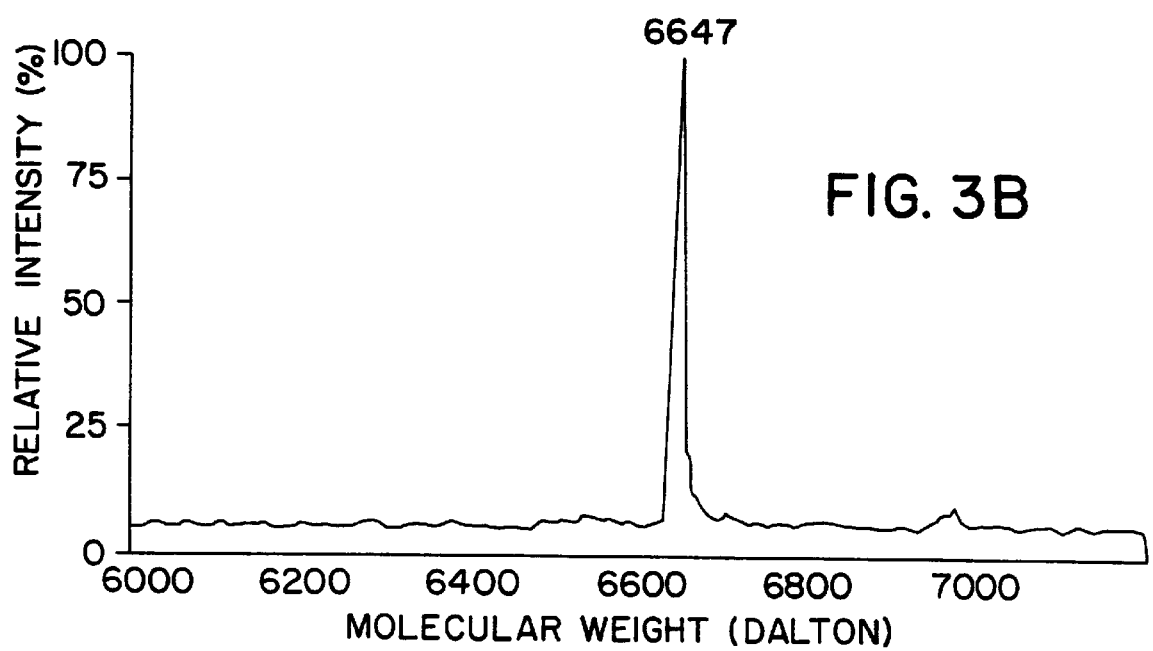

The desired product was readily purified by HPLC and was lyophilized to yield a white solid. This was characterized by ionspray mass spectrometry (FIG. 3) and was found to be the target 4-helix TASP 3 in high purity, and with the expected mass, i.e., the observed molecular weight was 6647.1±2.8 Daltons, while the calculated molecular weight for a monoisotopic $C_{288}H_{503}N_{82}O_{88}S_4$ is 6645.6 and the calculated molecular weight for $C_{288}H_{503}N_{82}O_{88}S_4$ having an average isotope composition is 6649.9. The ligated 4-helix TASP 3 was stable for days at ambient temperatures in pH 5.0 10 mM $NH_4OAc$, and was indefinitely stable at 4° C. at pH 6.0. Circular dichroism spectroscopy was used to determine the secondary structure of the ligated TASP molecule 3 in water. The molecule was highly helical (FIG. 4). Control studies of peptide 1 under identical conditions showed no helical content whatever. These conformational properties were similar to those observed for the closely related 4-helix TASP prepared by conventional means (supra). Ionspray MS under native conditions[17] showed that the 4-helix TASP occurred as a monomeric species, e.g., M. Baca et al. (*J. Am. Chem. Soc.*, 1992, vol. 114, pages 3992–3993).

The overwhelming feature of this synthetic approach is its simplicity. The ligation occurred rapidly in aqueous solution and essentially no other reaction products were detected. The product was readily purified to give exceptionally homogeneous material with a mass consistent with the proposed covalent structure. The observed helical secondary structure was consistent with the formation of the target 4-helix TASP molecule 3.

The major advantages of the chemoselective ligation approach include the elimination of microheterogeneity in the final product and the generality of the approach. Peptides simultaneously built up on the template by stepwise solid-phase synthesis yield very heterogeneous crude products. Mutter and co-workers have demonstrated the use of stringent chromatographic techniques to increase the purity of the final product (supra), but these protocols have not been applied to the larger and more hydrophobic ion channel assemblies prepared by Montal and co-workers (*Proc. Natl Acad. Sci. U.S.A.*, 1991, vol. 88, pages 6418–6422). Segment condensation of protected peptide fragments has been used to decrease heterogeneity but problems with solubility lead to extremely slow ligation reactions resulting in low yields. Recent work by DeGrado and co-workers used unprotected peptide fragments, but is of limited applicability due to the incompatibility of the ligation reaction with all functional groups, especially the $\epsilon$-amino group of lysine (*J. Am. Chem. Soc.*, 1992, vol. 114, pages 9656–9657).

In contrast to these approaches, the chemoselective ligation approach allows ready purification of the unprotected peptide components, which can be ligated at high concentration in a fast, clean reaction. The target compound is obtained directly in the final unprotected form and is readily purified. The method is of general applicability because the chemistry is compatible with all functional groups found in peptides and proteins (*Science*, 1992, vol. 256, pages 221–225). In previous work we have shown that purified unprotected peptides can be correctly ligated in solvents such as 6M guanidine·HCl or in organic/aqueous mixtures. This allows great flexibility in the selection of pro-helix sequences and of solvent conditions to maintain the necessary solubility for rapid reaction.

Materials and Methods:

Analytical and semipreparative gradient HPLC was performed on a Rainin dual pump high pressure mixing system with 214 nm UV detection using Vydac C-18 analytical (5 micron, 0.46×15 cm) and semipreparative (10 m, 1.0×25 cm) columns. Analytical runs used a 0%–67% B gradient over 30 min at 1mL/min where buffer A is 0.1% TFA in $H_2O$ and buffer B is 90% $CH_3CN$+10% buffer A. Mass spectra were obtained using a Sciex API-III quadrupole ion-spray mass spectrometer. CD measurements were obtained using an Aviv 62 DS instrument. Peptide concentrations were determined by amino acid analysis after hydrolysis in 6N HCl for 24 hours at 110° C.

Synthesis of pro-helix peptide 1. Except where noted, peptides were synthesized by manual stepwise solid phase methods according to published procedures, e.g., S. B. Kent (*Ann Rev Biochem.*, 1988, vol. 57, pages 957–989) and M. Schnolzer et al. (*Int. J. Peptide Protein Res.*, 1992, vol. 40, pages 180–193). Coupling yields were monitored by quantitative ninhydrin. The pro-helix was synthesized on a Gly thioester resin using standard $N^\alpha$Boc chemistry SPPS, e.g., J. Blake (*Int. J. Peptide Protein Res.*, 1981, vol. 17, pages 273–274) and D. Yamashiro (*J. Int. J. Peptide Protein Res.*, 1988, vol. 31, page 322). The peptide was deprotected and simultaneously cleaved from the resin by treatment with HF plus 2% anisole for 1 hour at 0° C. The crude peptide was taken up in neat TFA, diluted with ddH$_2$O to 0.5% TFA and lyophilized to remove residual anisole. The pro-helix was purified by semipreparative reversed phase HPLC (0%–67% buffer B over 60 min at 3 mL/min) and characterized by ionspray mass spectrometry, i.e., the observed molecular weight was 1372.2±0.4 Daltons while the calculated molecular weight is 1371.8 daltons (monoisotopic) or 1372.6 daltons (average isotope composition).

Synthesis of template peptide 2. The template peptide was synthesized using a combination of $N^\alpha$Boc-chemistry SPPS and $N^\epsilon$Fmoc lysine side chain protection on a Gly—OCH$_2$—Pam-resin (FIG 1B). To minimize the possibility of premature Fmoc removal, a separate brief neutralization with 5% diisopropylethylamine/DMF was used, rather than in situ neutralization in the coupling step, e.g., M. Schnolzer et al. (*Int. J. Peptide Protein Res.*, 1992, vol. 40, pages 180–193). Following nine synthetic cycles, the Fmoc protecting groups on the lysine side chains were removed by two 5 minute treatments with 50% piperidine/DMF. The free e-amino groups were bromoacetylated using bromoacetic acid/DIC coupling, e.g., R. A. Robey et al. (*Anal. Biochem.,* 1989, vol. 177, pages 373–377). The peptide was deprotected and cleaved by HF plus 10% p-cresol over 1 h at 0° C., using standard protocols, e.g., M. Schnolzer et al. (*Int. J. Peptide Protein Res.,* 1992, vol. 40, pages 180–193). The template was then purified to homogeneity by semipreparative reversed phase HPLC (25%–41% buffer B over 30 minutes at 3 mL/minute) and characterized by ionspray mass spectrometry, i.e., the observed molecular weight was 1482.7±0.4 Daltons while the calculated molecular weight is 1478.3 daltons (monoisotopic) or 1483.0 daltons (average isotope composition).

Synthesis of 4-helix TASP 3. Ligation was performed by combining 0.50 mg of the $(BrAc)_4$ template (Formula weight 1484 Daltons, $3.36 \times 10^7$ mole, 1.12 mM), and 2.75 mg pro-helix—$^\alpha$COSH (Formula weight 1372 Daltons, $2.0 \times 10^{-6}$ mole, 6.68 mM) in 300 μL of 10 mM $NH_4OAc$ aqueous buffer pH 5.0 at 23° C. Reaction was monitored by analytical reverse phase HPLC (4 μL aliquots). Peaks were collected based on UV absorbance and examined by ionspray MS, e.g., M. Schnolzer (*Anal. Biochem.,* 1992, vol. 204, pages 335–343). After 6.5 hours at 23° C., the reaction mixture was stored at 4° C. Product (170 μL of reaction mixture) was purified by reversed phase HPLC (38%–54% buffer B over 30 min at 3 mL/minute) and lyophilized giving 0.26 mg of pure product, theoretical yield: 1.27 mg, 20.5%. The mass was determined by ionspray mass spectrometry, i.e., the observed molecular weight was 6647.1±2.8 Daltons while the calculated molecular weight is 6645.6 daltons (monoisotopic) or 6649.9 daltons (average isotope composition).

Stability. Stability was monitored by analytical reversed phase HPLC and mass spectrometry of collected peaks. 1 mM 4-helix TASP from the ligation reaction was stored at 23° C. for several days without degradation. 5 mM 4-helix TASP stored in 100 mM Phosphate buffer pH 6.0 showed no decomposition after 7 days at 4° C.

Circular Dichroism. Both the pro-helix (7.5 μM) and the 4-helix TASP (1.78 μM) were dissolved in doubly distilled $H_2O$. Measurements were taken in a 2 mL cuvette with a path length of 1 cm at 20.0° C., scanning from 260 nm to 190 nm every 0.50 nm.

CONCLUSION

These results indicate the potential of the chemoselective ligation approach as a general route to the preparation of TASP-like macromolecules. Combinations of existing chemical tactics provide great versatility for the selective introduction of reactive moieties into unprotected peptide building blocks which can be used in the design and synthesis of a variety of TASP-related compounds. In particular, the thioester nucleophilic ligation chemistry described here can be combined with other ligation chemistries originally developed for rejoining fragments of proteins to generate a great diversity of nonlinear covalent molecular topologies, e.g., K. Rose et al. (*Bioconjugate Chem.,* 1991, vol. 2, pages 154–159) and H. Gaertner et al. (*Bioconjugate Chem.,* 1992, vol. 3, pages 262–268). In conjunction with modern analytical protein chemistry the chemoselective synthetic approach is a powerful adjunct to the design and study of conformations and activities of protein-related macromolecules.

---

What is claimed is:

1. A branched template assembled synthetic protein (TASP) having a dendritic linkage unit with a structure ψ(CO—S—CH$_2$—CO—NH).

2. A template assembled synthetic protein (TASP) as described in claim 1 further comprising:
   four dendritic linkage units having the structure ψ(CO—S—CH$_2$—CO—NH),
   four branch peptides, each of said branch peptides having a sequence $^+$NH$_3$—D—A—A—T—A—L—A—N—A—L—K—K—L—G—COS—, and
   a template peptide having a sequence $^+$NH$_3$—K(Ac—)—K($^+$NH$_3$)—K(Ac—)—P—G—K(Ac—)—E(COO$^-$)—K(Ac—)—G—COO$^-$,
   said four linkage units coupling said branch peptides to the four K(Ac—) residues of said template peptide.

3. An improved template assembled synthetic protein (TASP) having a branch peptide with a C-terminal end and a template peptide including an amino acid residue with a template side chain bearing an amino group, wherein the improvement comprises:
   a linkage unit having the structure ψ(CO—S—CH$_2$—CO—NH) coupling the C-terminal end of said branch peptide to said template peptide via the amino group of the template side chain as follows:

branch peptide-ψ(CO—S—CH$_2$—CO—NH)—template side chain
                                                  |
                                            template peptide, whereby the branch peptide serves as a branch upon the template peptide to form a template assembled synthetic protein (TASP).

4. An improved template assembled synthetic protein (TASP) as described in claim 3 wherein:
   the template side chain of said template peptide is a lysine side chain corresponding to a lysine amino acid residue.

5. An improved template assembled synthetic protein (TASP) as described in claim 3 wherein:
   said branch peptide is a pro-helical peptide which, upon incorporation into the template assembled synthetic protein (TASP) and exposure to helix promoting conditions, is capable of assuming a helical configuration.

6. An improved template assembled synthetic protein (TASP) as described in claim 3 wherein the branch peptide includes a first branch peptide and a second branch peptide, each with a C-terminal end, and the template peptide includes a first amino acid residue with a first template side chain bearing an amino group and a second amino acid residue with a second template side chain bearing an amino group, wherein the improvement further comprises:
   said linkage unit including a first linkage unit and a second linkage unit, each linkage unit having the structure ψ(CO—S—CH$_2$—CO—NH), the first linkage unit serving to couple the C-terminal end of said first branch peptide to said template peptide via the first template side chain and the second linkage unit serving to couple the C-terminal end of said second branch peptide to said template peptide via the second template side chain,
   whereby the first and second branch peptides serve as first and second branches upon the template peptide to form a template assembled synthetic protein (TASP) having two branches.

7. An improved template assembled synthetic protein (TASP) as described in claim 6 wherein:
   both said first and second branch peptides are pro-helical peptides which, upon incorporation into the template assembled synthetic protein (TASP) and exposure to helix promoting conditions, are capable of assuming helical configurations.

8. A process for preparing a template assembled synthetic protein (TASP) comprising the following steps:
   Step A: providing a template peptide including an amino acid residue having a template side chain bearing an amino group bonded to a haloacetyl functionality;
   Step B: providing one or more branch peptides, each of said branch peptides including a C-terminal end bearing an $^\alpha$COSH moiety; and then
   Step C: combining the template peptide from said Step A with one or more of the branch peptides of said Step B under nucleophilic reaction conditions for promoting a substitution reaction between the $^\alpha$COSH moiety of the branch peptides and the haloacetyl functionality of the template molecule for chemoselectivly ligating the branch peptides to the template peptide and forming the template assembled synthetic protein (TASP).

9. A process for preparing a template assembled synthetic protein (TASP) as described in claim 8 wherein:

in said Step A, the haloacetyl functionality is a bromoacetyl functionality.

10. A process for preparing a template assembled synthetic protein (TASP) as described in claim 9 wherein:

in said Step A, the template side chain bearing the amino group bonded to the haloacetyl functionality is a lysine side chain corresponding to a lysine amino acid residue.

11. A process for preparing a template assembled synthetic protein (TASP) as described in claim 8 wherein:

in said Step C, the C-terminal end of the branch peptide being ligated to the amino acid residue of the template peptide by means of a linkage unit having the structure $\psi(CO-S-CH_2-CO-NH)$ to form the template assembled synthetic protein (TASP).

12. A process for preparing a template assembled synthetic protein (TASP) as described in claim 8 wherein:

in said Step B, the branch peptides are pro-helical peptides which, upon incorporation into the template assembled synthetic protein (TASP) and exposure to helix promoting conditions, are capable of assuming a helical configuration; and then, after or concurrent with Step C, Step D: exposing the formed template assembled synthetic protein (TASP) of said Step C to helix promoting conditions for promoting the formation of helices by the branch peptides.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: Thiolester-bond
        ( B ) LOCATION: 14
        ( D ) OTHER INFORMATION: /label=COS
            / note= "COS indicates a thioester group on the C-terminal amino acid."

( x i ) SEQUENCE DESCRIPTION: SEQ ID NO:1:

Asp Ala Ala Thr Ala Leu Ala Asn Ala Leu Lys Lys Leu Gly
    1                5                            10

( 2 ) INFORMATION FOR SEQ ID NO:2:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide

```
(ix) FEATURE:
      (A) NAME/KEY: Modified-site
      (B) LOCATION: 1
      (D) OTHER INFORMATION: /label=Ac
            / note= "K(Ac) represents a lysine amino acid
            residue having an lysine side chain with an
            acetylated amino group."

(ix) FEATURE:
      (A) NAME/KEY: Modified-site
      (B) LOCATION: 8
      (D) OTHER INFORMATION: /label=Ac
            / note= "K(Ac) represents a lysine amino acid
            residue having an lysine side chain with an
            acetylated amino group."

(xi) SEQUENCE DESCRIPTION: SEQ ID NO:2:

Lys  Lys  Lys  Pro  Gly  Lys  Glu  Lys  Gly
1                   5
```